US007645140B2

(12) United States Patent
Duffy et al.

(10) Patent No.: US 7,645,140 B2
(45) Date of Patent: Jan. 12, 2010

(54) METHOD FOR ASSESSING NAVIGATIONAL CAPACITY

(75) Inventors: Charles J. Duffy, Pittsford, NY (US); Laura Cushman, Rochester, NY (US); Mark Mapstone, Pittsford, NY (US)

(73) Assignee: University of Rochester Medical Center, Rochester, NY (US)

( * ) Notice: Subject to any disclaimer, the term of this patent is extended or adjusted under 35 U.S.C. 154(b) by 951 days.

(21) Appl. No.: 10/703,101

(22) Filed: Nov. 5, 2003

(65) Prior Publication Data

US 2004/0175683 A1 Sep. 9, 2004

Related U.S. Application Data

(60) Provisional application No. 60/424,157, filed on Nov. 5, 2002.

(51) Int. Cl.
*G09B 19/00* (2006.01)
(52) U.S. Cl. ..................................... 434/236
(58) Field of Classification Search ................ 434/236
See application file for complete search history.

(56) References Cited

U.S. PATENT DOCUMENTS

| 4,207,087 A * | 6/1980 | Morrison et al. ............... 463/9 |
| 4,453,732 A * | 6/1984 | Assanah et al. ............. 280/648 |
| 6,045,515 A | 4/2000 | Lawton |
| 6,364,845 B1 * | 4/2002 | Duffy et al. .................. 600/558 |
| 6,599,129 B2 * | 7/2003 | Jenkins et al. .............. 434/169 |
| 6,688,746 B2 | 2/2004 | Malov |

OTHER PUBLICATIONS

Janke, Mary K.; "Age Related Disabilities that May Impair Driving and Their Assessment"; Jul. 1994.*
Montello, Daniel R.; "Spatial Orientation and the Angularity of Urban Routes"; Environment and Behaviour, vol. 23, No. 1, 47-69 (1991).*
Monacelli et al., "Spatial disorientation in Alzheimer's disease—The remembrance of things passed," *Neurology*, 61:1491-1497 (2003).

* cited by examiner

*Primary Examiner*—Xuan M Thai
*Assistant Examiner*—Timothy Musselman
(74) *Attorney, Agent, or Firm*—Townsend and Townsend and Crew LLP (57) ABSTRACT

A method for assessing the navigational capacity in human subjects, and its use in diagnosing spatial disorientation in neurodegenerative diseases, such as, for example Alzheimer's disease. The method for assessing the navigational capacity includes conducting a spatial orientation test, recording the results of the test, analyzing the test results and making a determination of the navigational capacity of a human subject. In its most simple sense, navigational capacity includes the capacity not to get lost. The spatial orientation test includes various naturalistic navigation tasks that are each designed to assess specific areas of the navigational capacity of a subject.

23 Claims, 4 Drawing Sheets

METHOD FOR ASSESSING NAVIGATIONAL CAPACITY

CROSS-REFERENCES TO RELATED APPLICATIONS

This application claims the benefit of U.S. Provisional Patent Application No. 60/424,157, filed Nov. 5, 2002, which application is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made in part with Government support under the National Institute of Health ("NIH") grant EY10287 to Dr. Charles J. Duffy, NIH training grant T32EY07125 to the Center for Visual Sciences and NIH grant AG08665 to the Alzheimer's Disease Center at the University of Rochester. The U.S. government may have certain rights in the invention.

BACKGROUND OF THE INVENTION

The present invention relates to methods for assessing navigational capacity and to their use in diagnosing spatial disorientation in neurodegenerative diseases.

It is known that Alzheimer's disease (AD) is characterized by memory loss in the setting of other progressive behavioral and cognitive impairments. It is also known that spatial disorientation affects more than one-third of AD patients early in the illness {Henderson}. Spatial disorientation is disabling because it impairs independent navigation and interferes with the capacity to drive safely and maintain a separate household.

Spatial orientation relies on the integration of perceptual cues about location and self-movement. Location cues orient the observer by relating recognized landmarks to remembered positions in a spatial framework that defines their proximity to other landmarks. Self-movement cues orient the observer relative to a starting position by tracking successive movements through path integration. Orientation by landmarks relies on access to a long-term cognitive map of the environment, whereas orientation by self-movement is independent of the observer's familiarity with a site.

In mammals, cognitive mapping is attributed to the hippocampus where individual neurons represent particular locations in the environment. As the hippocampus is involved early in the course of AD, it is likely that orientation by landmarks might suffer early impairment and leave patients relying on path integration. As path integration might fail, these patients are left suffering spatial disorientation.

The present inventors have shown previously that spatial disorientation in AD is related to impaired ability to see the patterned visual motion of optic flow that supports self-movement perception and orientation by path integration.

To help characterize navigational capacity, methods are needed that test the relationship between remembered locations and spatial orientation in human subjects, especially those suffering from neurodegenerative diseases such as AD.

BRIEF SUMMARY OF THE INVENTION

The present invention is directed towards a method for assessing the navigational capacity in human subjects, and its use in diagnosing spatial disorientation in neurodegenerative diseases, such as, for example AD. The method for assessing the navigational capacity includes conducting a spatial orientation test, recording the results of the test, analyzing the test results and making a determination of the navigational capacity of a human subject. In its most simple sense, navigational capacity includes the capacity not to get lost. The spatial orientation test includes various naturalistic navigation tasks that are each designed to assess specific areas of the navigational capacity of a subject.

In one embodiment, the method for assessing the navigational capacity in a human subject includes taking the subjects on a course of a predetermined path in an environment, wherein the path comprises a plurality of turning points. The method further includes conducting a spatial orientation test comprising asking the subject questions concerning the path; recording the subject's response to the questions as a test score; analyzing the test score to obtain analyzed result; and assessing the subject's navigational capacity using the analyzed result.

In certain embodiments, the subject is taken on the predetermined path while the subject is seated in a wheeled chair.

In one aspect, the spatial orientation test includes a route-learning test. For the route-learning test, after completing the initial route, the taking of the route is commenced a second time. Participants are asked whether they had gone left, right or straight at each of various choice points. Mistakes are recorded and participants are corrected to maintain the integrity of the path.

In another aspect, the spatial orientation test includes an object recall test. For the object recall test, the subject is asked to name only those objects or fixtures that were helpful in finding the subject's way on the self-directed, second trip through the course. The number of objects listed is used as a dependent measure in analysis.

In another aspect, the spatial orientation test includes a free recall test. For the free recall test, after the second trip around the route, participants are given a set time period (e.g., 1 min.) to name as many objects or landmarks as they could recall from the trip. This score for this test includes the total number of items and their order with respect to the sequence in which items were encountered on the path.

In another aspect, the spatial orientation test includes a self-orientation test. For the self-orientation test, while seated at the starting/finishing point, participants are shown pictures of various (e.g., ten) different objects or locations taken from the test route. They are asked to point in the direction of the location as if there were no walls between themselves and the target. Responses are scored as correct if they pointed in the correct general direction (e.g., +/−22.5°). The picture presentation sequence may be randomized.

In another aspect, the spatial orientation test includes a route drawing test. For the route drawings test, after moving the participant to a quiet area adjacent to the testing environment, they are asked to draw the route one segment at a time. A drawn-to-scale outline of the test environment is provided, a main landmark is pointed-out, and participants are asked to mark the starting point. The next test environment outline includes the correct starting point, and participants are asked to draw a line from the starting point to show the first segment of the trip (to the next choice point). This is done several times until the subject has completed the drawing of the path in its entirety on a final scaled outline.

In another aspect, the spatial orientation test includes an image recognition test. For the image recognition test, several (e.g., ten) still images are presented to the subject. A portion (e.g., five) of the images is from the subject's view of the test path and another portion (e.g., five) is from comparable view of locations other than the test path. Responses are scored as correct depending on whether each picture is correctly identified as being from the test path or not.

In another aspect, the spatial orientation test includes an image location test. For the image location test, a second set of still images from the participant's view of the test path are presented to the subject. The subject is given a drawn-to-scale outline of the environment that included a letter and an arrow corresponding to the location of each photo. The subject is told that the pictures were taken, "as if you were sitting on the letter and looking in the direction of the arrow." A starting point landmark is pointed-out, and the subject is asked to match each image with its respective letter. Responses are kept independent and scored as number correct without feedback.

In another aspect, the spatial orientation test includes a video location test. For the video location test, several (e.g., ten) short video clips taken from the subject's view of the test path is presented to the subject. After each video clip, the subject is asked to draw an 'x' on a blank map where the clip began and an arrow coming from the 'x' showing where the rider was moving in the clip, and where the clip ended. The clips may be viewed several (e.g., 3) times each.

In another aspect, the method for assessing the navigational capacity of a subject includes correlating the results of the test with a profile for a neurodegenerative disease, such as for example, Alzheimer's disease.

These and other embodiments of the present invention, as well as its advantages and features, are described in more detail in conjunction with the description below and the attached figures.

DETAILED DESCRIPTION OF THE INVENTION

Embodiments of the present invention are directed towards methods for assessing the navigational capacity in human subjects, and their use in diagnosing spatial disorientation in neurodegenerative diseases, such as, for example AD. The method for assessing the navigational capacity includes conducting a spatial orientation test, recording the results of the test, analyzing the test results and making a determination of the navigational capacity of a human subject. In its most simple sense, navigational capacity includes the capacity not to get lost.

Figure 1:
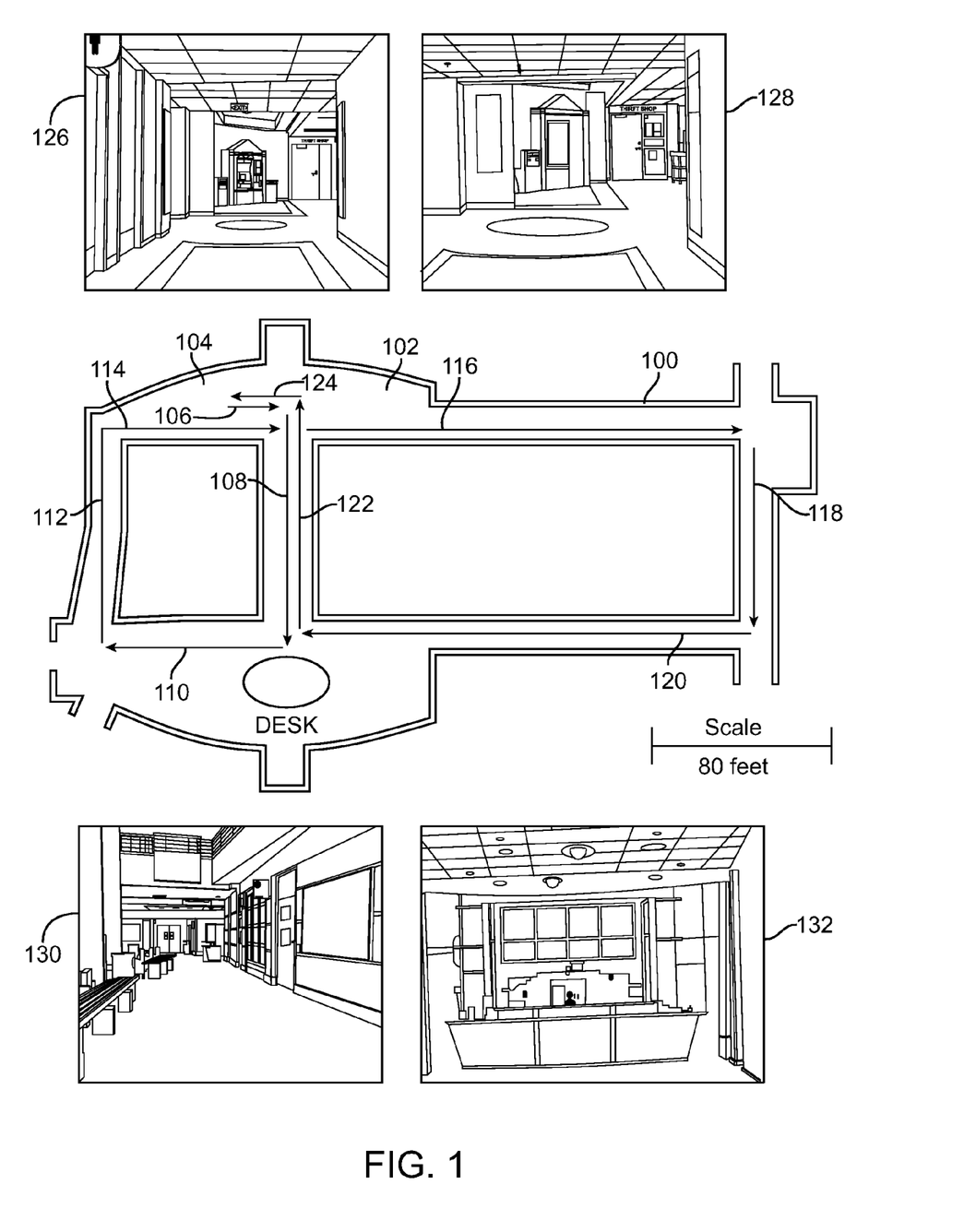
FIG. 1 is a diagram of a predetermined path in an environment that is used to assess the navigational capacity of a human subject.

The spatial orientation test includes various naturalistic navigation tasks that are each designed to assess specific areas of the navigational capacity of a subject. Each of these various tests is described below in further detail. First, a specified route was chosen. Such a route is shown on FIG. 1. FIG. 1 shows a scaled drawing of an environment 100 through which a predefined path 102 has been chosen. As is shown in FIG. 1, the path 102 includes a starting point 104, a predefined path 102 having a plurality of segments (106-124), and a plurality of turning points at the beginning or ending point if each segment. Participants were taken on the specified route and later asked questions about the path and the environment. Testing began at a standard starting point with the subjects seated in a wheelchair. They were instructed to attend to the route, as they would later be asked to retrace the route and undergo testing related to it. Participants were then pushed along a path (e.g., 1000 ft path) over a time period (e.g., 4 min.). No further cueing or discussion took place until the route was completed. On completion of the route, various tests were administered to assess knowledge concerning the route, with each subtest consisting of various questions. In one embodiment, eight tests were administered and each test consisted of ten questions. Further, in one embodiment the tests were administered in the ordered described below. However, the methods in accordance with the embodiments of the present invention may include the performance of any other subset of these eight tests which may be administered in any order.

Route Learning Test: After completing the initial route, the route was begun a second time. Participants are asked whether they had gone left, right or straight at each of various (e.g., 10) choice points. Mistakes are recorded and participants were corrected to maintain the integrity of the path.

Free Recall Test: After the second trip around the route, participants are given a set time period (e.g., 1 min.) to name as many objects or landmarks as they could recall from the trip. The answers are scored as correct as the total number of items and their order with respect to the sequence in which items were encountered on the path.

Self-Orientation Test: While seated at the starting/finishing point, participants are shown pictures of various (e.g., ten) different objects or locations taken from the test route. They are asked to point in the direction of the location as if there were no walls between themselves and the target. Responses are scored as correct if the subject pointed in the correct general direction (e.g., +/−22.5°). The picture presentation sequence may be randomized.

Route Drawing Test: After moving the participants to a quiet area adjacent to the testing environment, they are asked to draw the route one segment at a time. A drawn-to-scale outline of the test environment was provided, a main starting point landmark desk is pointed-out, and participants are asked to mark the starting point. The next test environment outline includes the correct starting point, and participants are asked to draw a line from the starting point to show the first segment of the trip (to the next choice point). This process is repeated several times (e.g., ten times) to complete the drawing of the entire route.

Object Recall Test: Participants are asked to name only those objects or fixtures that were helpful in finding their way on the self-directed, second trip through the course. The number of objects listed was used as a dependent measure in analysis.

Image Recognition Test: Several (e.g., ten) still images are presented to the participants. The presentation may be a computer-based presentation (e.g., a presentation such as PowerPoint). Examples of these still images are shown on FIG. 1 (128-132). A portion (e.g., five) of the images is from the participant's view of the test path and another portion (e.g., five) is from a comparable view of locations other than the test path. Responses were scored as to whether each picture was correctly identified as being from the test path or not.

Image Location Test: A second set of still images from the participant's view of the test path are presented to the participants. The presentation may be a computer-based presentation. Participants are given a drawn-to-scale outline of the environment that includes a letter and an arrow corresponding to the location of each photo. They are told that the pictures were taken, "as if you were sitting on the letter and looking in the direction of the arrow." A starting point landmark is pointed-out, and participants are asked to match each image with its respective letter. Responses are kept independent and scored as number correct without feedback.

Video Location Test: Several (e.g., ten) short video clips taken from the participant's view of the test path are presented to the participants. The presentation may be a computer-based presentation (e.g., PowerPoint). After each video clip, participants are asked to mark on a blank map where the clip began and an arrow coming from the starting mark showing where the rider was moving in the clip, and where the clip ended. The clips may be viewed up to several (e.g., 3) times each.

The utility and effectiveness of the spatial orientation test(s) were demonstrated by administering the tests based on the following methodology. Four participant groups were used in this study: young normal (YN, n=47, mean age+/−sd=23.5+/−5.9), middle age (MA, n=24, age=51.8+/−4.9), older adults (OA, n=26, age=73.0+/−7.6) and Alzheimer's disease (AD, n=14, age=73.4+/−5.9). There was no difference in age between OA and AD groups. Mini-Mental Status Exam (MMSE) scores were: YN=29.3+/−1.1, MA=29.7+/−0.5, OA=28.7+/−1.4, and AD=23.1+/−3.3.

For one study, all participants were community-dwelling: YN participants were undergraduate or graduate students. The MA group included volunteers from the University of Rochester community. The OA group consisted of AD patient's spouses or caregivers. AD patients were recruited from the clinical programs at the Medical Center.

The participants were free of neurological, ophthalmic, and psychiatric illness other than the defining illness in the AD group. Corrected binocular visual acuity of 20/40 and an MMSE score>17 was required. All AD participants were diagnosed by a geriatric neurologist or psychiatrist specializing in dementia and met NINCDS-ADRDA criteria for probable AD.

Each participant first gave informed consent in protocols approved by the University of Rochester Medical Center's Research Subjects Review Board. All tests were administered in the Visual Orientation Laboratory or the main lobby at the Medical Center. Testing was typically completed in two 90-minute sessions on two days as detailed below:

Basic visual function All participants underwent Snellen visual acuity testing to confirm binocular acuity of at least 20/40. Contrast sensitivity was tested at five spatial frequencies (0.5-18 cycles/°, VisTech Consultants, Inc.). Contrast sensitivities were in the normal range for all groups. YN participants performed better than the other three groups, but there were no significant differences among the three other groups.

Neuropsychological tests The neuropsychological battery assessed general cognitive ability, spatial orientation, verbal and non-verbal memory. The Money Road Map test assesses topographic orientation in simulated route following with participants using a pencil to trace a pre-drawn path on a village map and report whether turns are to the traveler's left or right. Two test were taken from the Wechsler Memory Scale—Revised: the Figural Memory test uses block patterns in an immediate visual recognition task; the Verbal Paired Associates Test I has immediate and delayed recall sub-test of memory for a list of word pairs. Categorical Name Retrieval, Facial Recognition, and Judgment of Line Orientation tests were also administered. The Mini-Mental State Examination (MMSE) was used only to assign subjects to a group.

Next, the spatial orientation tests as described above were administered. As set forth above, participants were taken on a specified route through an environment and later asked questions about the path and the environment. Testing began at a standard starting point with the subjects seated in a wheelchair. They were instructed to attend to the route, as they would later be asked to retrace the route and undergo testing related to it.

Participants were then pushed along the path over a time period (e.g., 4 minutes). No further cueing or discussion took place until the route was completed. On completion of the route, various tests as described above were administered to assess knowledge concerning the route, each subtest consisting of various (e.g., 10) questions.

In addition to the initial battery of tests, re-testing was performed. For the retesting, a random subset of participants in each group (31 YN, 13 MA, 9 OA and 5 AD) were re-tested on the entire navigational task within 48 hours of their initial test.

After the completion of the test, the data was analyzed. In one embodiment of the data analysis, the total test score is the sum of scores on the eight major sub tests (maximum of 80) and was used as a dependent measure. A maximum score of 10 was used as a perfect score in both the Free Recall and Object Recall tests. In one embodiment, the spatial orientation tests and the data analysis can be carried out at a spatial orientation laboratory set up to carry out the methods of the embodiments of the present invention. An example of such a laboratory is described in U.S. Pat. No. 6,364,845, Entitled: "Methods for diagnosing visuospatial disorientation or assessing visuospatial orientation capacity," the disclosure of which is herein incorporated by reference in its entirety for all purpose.

Dependent measures from the neuropsychological testing included the MMSE score (maximum score=30), Money Road Map (max=32), WMS-R Figural Memory (max=10), Verbal Immediate Memory (max=24), Verbal Delayed Memory (max=8), Line Orientation (max=30), Facial Recognition (max=45), and animals named in 1 min of category name retrieval.

Results from the navigational and neuropsychological tests were analyzed using multivariate ANOVA (MANOVA) analyses to test for significant differences between subject groups. All significant main effects were followed-up with step-down one-way ANOVAs and post-hoc tests using Tukey's HSD. All alpha levels for statistical significance were $p<0.05$. Additional analyses included correlations, Linear Regression (to examine the relationship between the navigational and neuropsychological scores) and factor analysis of the navigation test scores. All statistical analyses were run using SPSS statistical software (SPSS, Inc.).

Figure 2A:
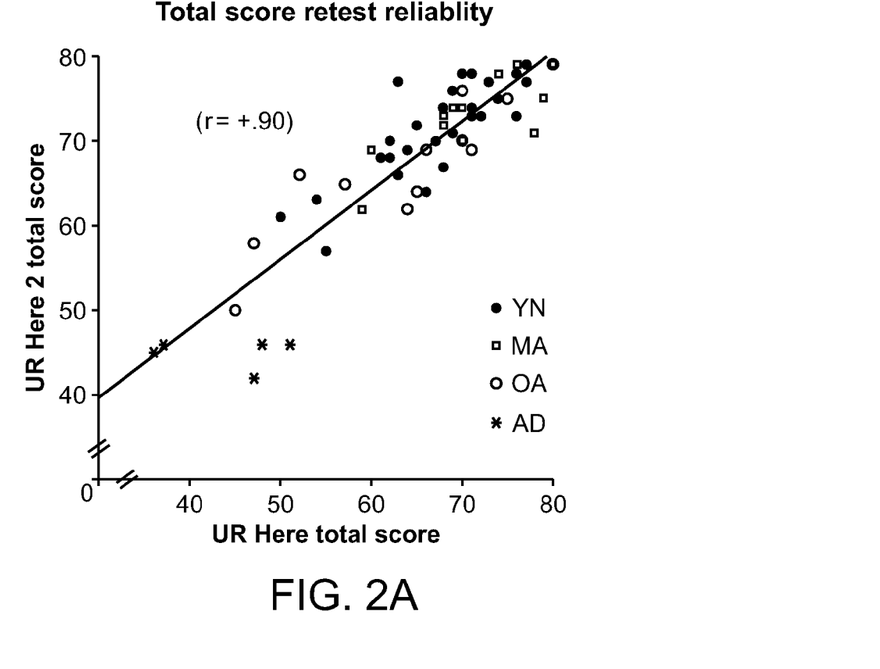
FIG. 2A is a graph showing the reliability of the tests used to assess the navigational capacity of a human subject.

After the data analysis, the following results were obtained. The psychometric properties of the spatial orientation test were addressed by conducting a formal assessment of test-retest reliability, using data from all participants. A within-participants correlation was computed using test scores obtained at the time of the first administration, and again at the second or the re-test administration of the test. A test-retest correlation of 0.93 was obtained as is shown in FIG. 2A. This figure (FIG. 2A) shows the first (abscissa) and second (ordinate) test scores for all subjects. A correlation between the two scores yielded a test-retest reliability coefficient of greater than 0.9 (0.93), which indicates a superior reliability for a behavioral test. This substantial correlation, well within the range recommended for behavioral and neuropsychological tests, suggests that test scores are replicable and not unduly influenced by extraneous factors.

Figure 2B:
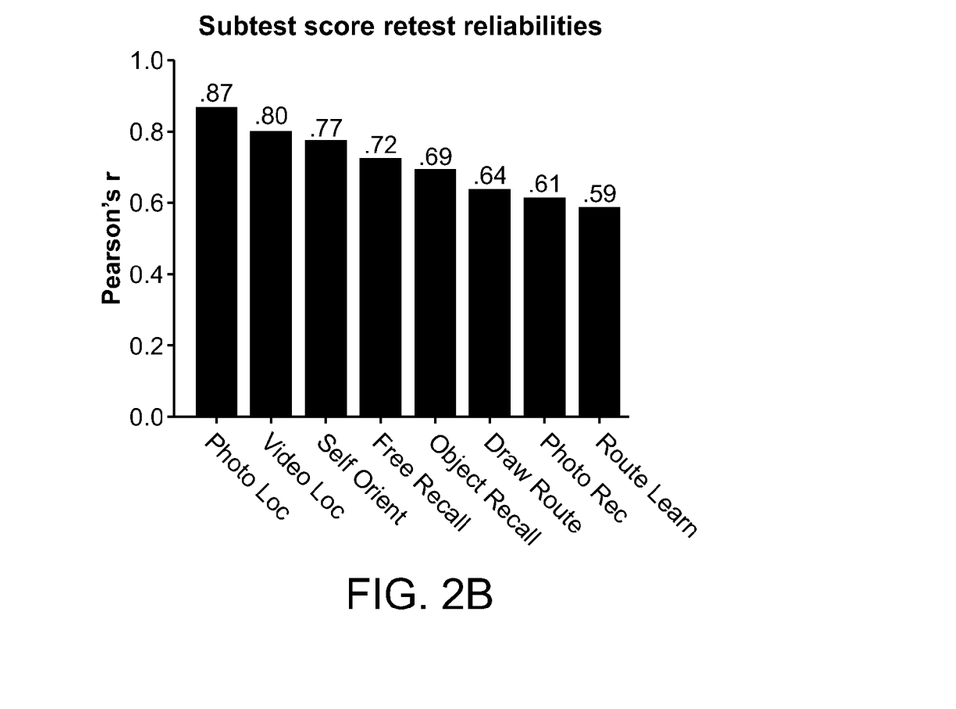
FIG. 2B is bar graph showing the test-retest reliability coefficients for the various tests used to assess the navigational capacity of a human subject.

The reliabilities for each of the individual test is seen in FIG. 2B. Each of the groups evidenced slight improvement on the second administration, including the AD group (sign test, p<0.05). The YN, MA, and AD groups gained approximately 2 points on their total score, on average, and the OA group gained 5 points. There were no significant correlations between visual acuity, contrast sensitivity or gender and overall navigational capacity performance. As can be seen in FIG. 2B, the most reliable tests were those related to visuospatial perception supporting the location of scenes from the path, with little change in performance after repeated exposure.

Figure 3A:
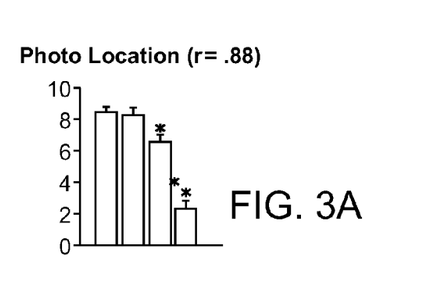
FIGS. 3A-I are bar graphs showing the results for various tests used to assess the navigational capacity of four different groups of human subjects.
Figure 3B:
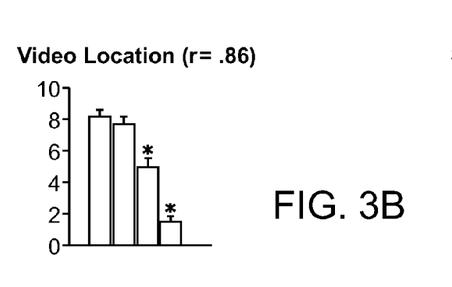
Figure 3C:
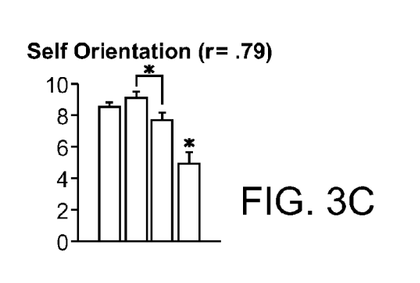
Figure 3D:
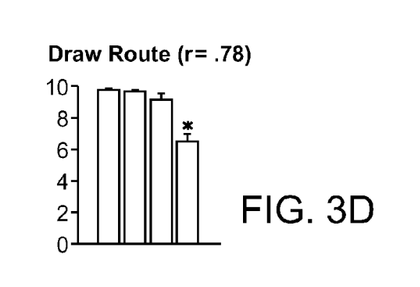
Figure 3E:
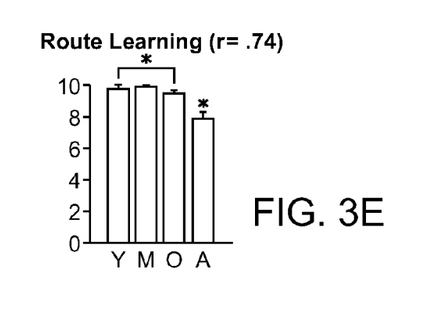
Figure 3F:
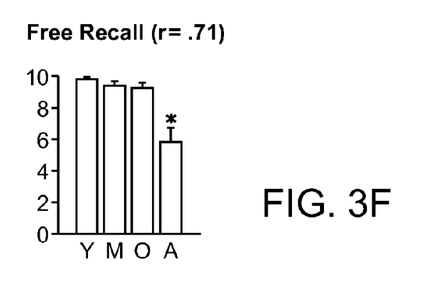
Figure 3G:
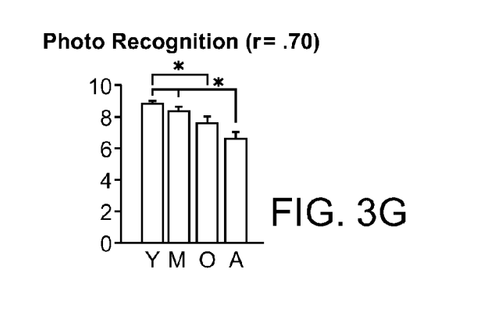
Figure 3H:
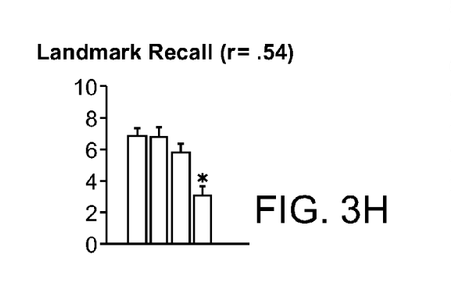
Figure 3I:
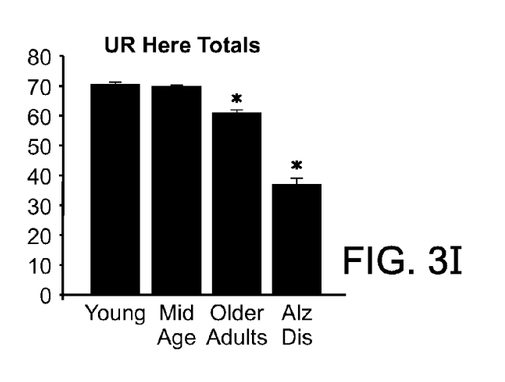

Each group's mean total score on the spatial orientation test was analyzed using a one-way ANOVA between groups. The performance of the AD group was significantly lower than that of the other groups, as is shown in FIG. 3I. The OA group performed at a lower level than the 2 younger groups, but better than the AD group. The two youngest age groups (YN, MA) did not differ from one another. It may be concluded that the total spatial orientation test scores were sensitive to both age and disease effects.

A two-way ANOVA showed both group and task effects on the spatial orientation test ($F(3,97)=50.3$, $p<0.001$; $F(7,91)=53.6$, $p<0.001$). This was followed by a series of one-way ANOVAs and post hoc comparisons. The performance of each subject group on the eight subtests is seen in FIG. 3A-H. The AD group performed significantly poorer than all other groups on all subtests. On the photo location and video location subtests, OA participants had lower scores than both the YN and MA groups. On the photo recognition subtest, the older adult (OA) participants scored significantly lower than the young normal (YN) participants. However, OA subjects performed at the same level as other normal subjects on the route learning and route drawing subtests.

A stepwise multiple regression analysis (with all participants included) was performed to assess the relative contribution of various subtests to the total score. Photo location (FIG. 3A), as the first item in a stepwise regression, has an $R^2$ value; the tasks in FIGS. 3B-H show $r^2$ values. As indicated by the r values and their order in FIG. 3A, the image location, video location and self-orientation tests subtests contributed most to overall spatial orientation test performance; together they explained 92% of the variance. Factor analysis of the test battery yielded a three-factor solution. All of the test loaded on some factors with loadings greater than or equal to 0.7. Video location and image location loaded on nearly the same factor.

Figure 4A:
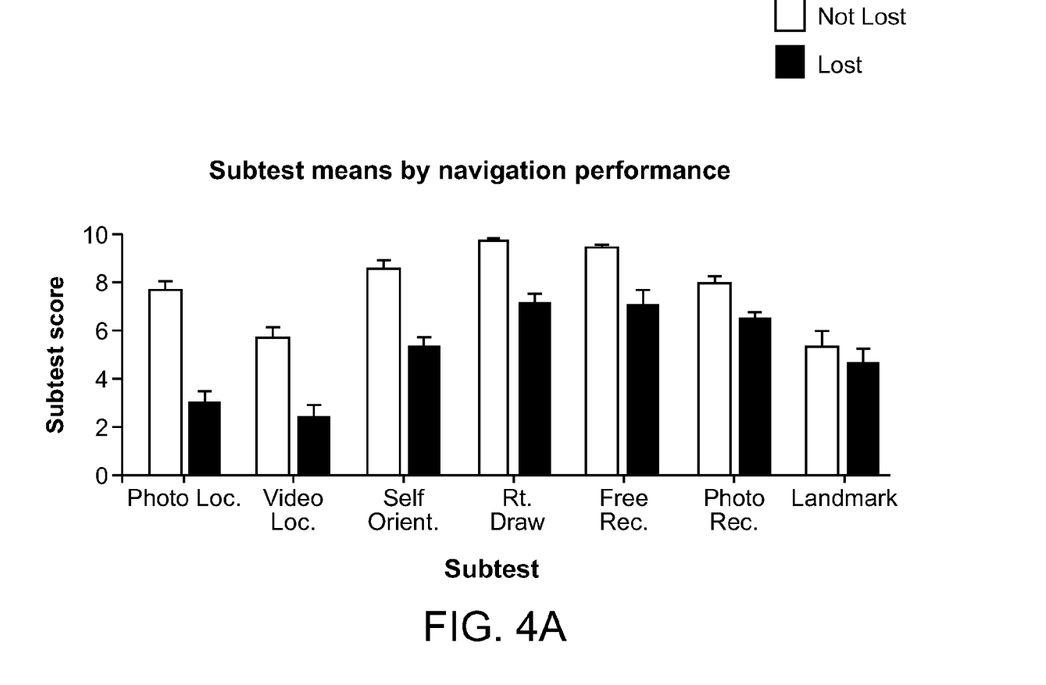
FIG. 4A is a bar graph showing the test score means by navigational performance.
Figure 4B:
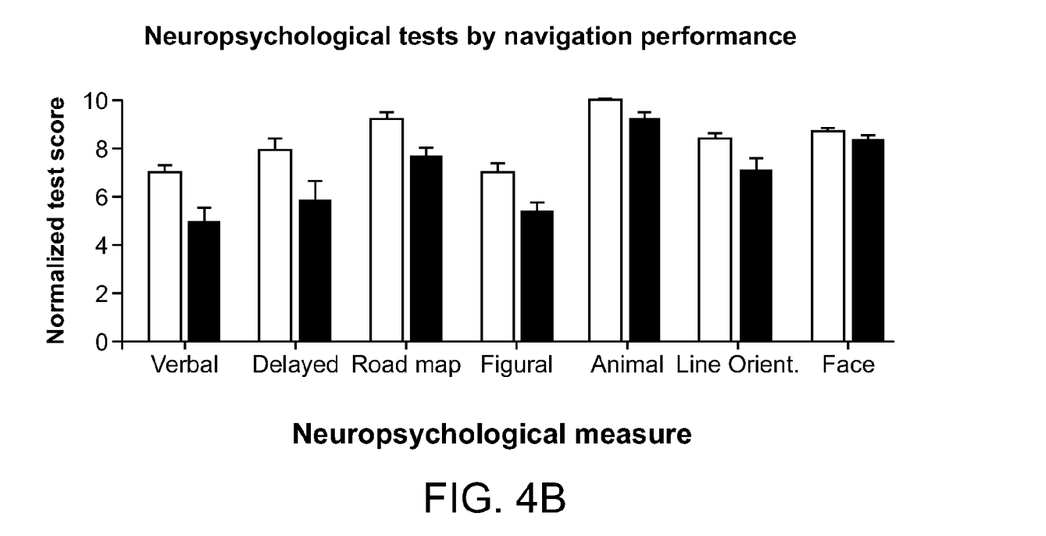
FIG. 4B is a bar graph showing the results of neuropsychological tests by navigational performance.

Next, similar analyses were done separately by group as is shown in FIG. 4A-B. Groups as is used in FIG. 4A-B consist of lost and not lost groups. FIGS. 4A-B uses errors made on the route learning test to define and separate subjects who did get (or would have gotten) lost from those who did not. All subjects in the OA and AD groups who made at least one wrong turn on the route learning test comprises the "lost" group. The mean performance of those lost versus not lost groups on each test is illustrated in FIG. 4A. FIG. 4B compares the neuropsychological test performance of these same two (i.e., lost or not lost) groups.

The largest contribution to total score variance among young and middle age subjects were from the video and image location subtests. Since these subjects performed well overall, it appears that only those tasks requiring a mental link between scenes and locations presented any difficulty. The image (or photo) location subtest explained the greatest amount of variance for the older group as well. A very different pattern is seen in the AD group, which performed very poorly on all subtests. The route drawing task suddenly emerged as contributing the greatest amount of variance. Another way to view this is that some members of the group were able to perform this simpler task, creating greater variability and a strong relationship to the overall score. This task may represent AD subjects' ability to identify some overall sense of the path they had traveled along the route.

A qualitative analysis of the photo recognition test by group was done to establish the proportion of false positive and false negative errors made. An interesting pattern emerged, with young control subjects having a false positive ratio of 0.33 of errors made, and AD subjects having a ratio of 2.57. This clearly suggests AD subjects could not distinguish novel or unique stimuli as such. The index of false positive errors nearly doubled in each successive age group from young to middle age, older and AD groups. The proportion of false positive errors was consistent across groups.

To assess the underlying components of the spatial orientation test in a different way, a principal components factor analysis was performed using data from all participants. Two factors emerged from this analysis. Six of the subtests clustered on a single factor that explained the greatest amount of total variance. These included: Route learning, self-orientation, drawing the route, photo recognition, and photo location and video location. These tasks all related to the spatial navigation nature of the task, and together explained 43 percent of the total variance in spatial orientation test scores.

A second factor emerged which consisted of two free recall tasks (free recall and object recall) administered at different points during the spatial orientation test. These tasks accounted for only an additional 15 percent of the total variance, and likely reflect a general memory factor. The same two-factor solution emerged using only normal subjects. In a separate analysis, free recall test responses (omitting the first response) were scored one point if the object named literally followed the previous one on the actual route. A ratio was then calculated from the total of such responses divided by the total number of responses. This created an index of spontaneous consecutive recall. The AD group had extremely few such consecutive responses (approximately 1%). Of the few objects AD participants recalled in general, qualitative analysis indicated that they tended to be items visible at the time. The other groups not only remembered many more objects, but approximately 30% were consecutively ordered, possibly indicating a mental map of the route.

Another matter concerns the relationship of spatial orientation test to more conventional neuropsychological tests, especially those known to relate to visual-perceptual abilities. A stepwise multiple regression analysis (with all normal participants) was used to see how well a combination of neuropsychological measures could predict (account for variance in) spatial orientation test scores. The best-fitting model included 5 of the neuropsychological measures, the Verbal Paired Associates (memory) test ($r^2=$), Judgment of Line Orientation test ($r^2=$), Animal naming ($r^2=$), the Road Map test ($r^2=$), and the Figural Memory subtest (Weschler Memory Scale) ($r^2=$). Together, these variables accounted for 63% of the variance in spatial orientation test scores. This reflects a degree of overlap, as would be expected, but also the fact that a significant portion of unique variance remains. This variance, unaccounted for by the other measures, likely represents the unique aspects and contribution of spatial orientation test in accordance with the embodiments of the present invention.

The relationship of neuropsychological tests to the spatial orientation test was also examined separately by group. There was a significant group effect overall ($F(3,97)=8.22$, $p<0.0001$). Only 1 to 3 tests significantly correlated with the spatial orientation test scores in any group. The conventional neuropsychological tests do not explain the spatial orientation test scores well, even though there are some expected correlations. The spatial orientation test was designed and appears to tap abilities related to navigational skills that are only modestly tapped by conventional tests, even those with a strong perceptual or spatial focus.

Correlational analyses also revealed significant relationships between total spatial orientation test scores and these neuropsychological tests. The three tests with the highest, statistically significant single-order correlations were: the Road Map test ($r=0.51$), the Figural Memory subtest ($r=0.43$), and the Judgment of Line Orientation test ($r=0.46$). The correlations between these measures and the spatial orientation test underscore the fact that the spatial orientation test is measuring relevant capacities, i.e. what it was intended to, an element of convergent validity. All of the measures noted above are primarily related to visual-spatial cognitive operations. The fact that correlations with verbal memory measures or MMSE scores were substantially lower or non significant pertains to divergent validity, or the fact that the methods of assessing navigational capacity in accordance with the embodiments of the present invention are not primarily measuring verbal memory or gross cognitive capacity.

The embodiments of the present invention provide a novel, real-world navigation test. The test developed has several unique properties. The tests were administered in a real-life setting, and was readily understood by participants. The tasks could be performed by AD participants as well as by normal controls. Route finding was done by following a previously experienced route, not a map. By allowing participants to be pushed in a wheelchair, discomfort or other problems with ambulation were minimized. The tasks involved several measures of object or spatially-based incidental learning, not just route finding.

The spatial orientation test in accordance with embodiments of the present invention is complex because of its many test components. It is therefore desirable to demonstrate its reliability, a psychometric feature not frequently considered. The overall reliability of spatial orientation test is rather good and similar to many standardized behavioral tests. The various tests, with fewer items, would be expected to show lower individual reliabilities, but the results described above are still reasonable. Similarly, the slight improvement in scores with repeat testing was expected. It was interesting that even the AD group showed mild improvements, possibly suggesting preserved functioning of relevant implicit memory processes.

In terms of overall performance on the spatial orientation test, the AD group did worse on all tests relative to the other groups. However, the level of performance did vary across the various tests and was not simply a series of floor effect scores. It is of note that the AD group did best in terms of being able to duplicate the overall route on the route finding task.

The OA group most often performed at an intermediate level between the AD and younger participants. This can be seen as consistent with aging effects on both visual-spatial tasks as well as learning and memory tasks. However, OA participants could reproduce the route both in real space and in drawing at a level equal to both younger groups.

Three of the tests were found to account for virtually all the variance in the spatial orientation battery. These were the image or photo location, video location and self-orientation tests. These tests share in common the operation of placing a visual object or scene (photo) in a specific spatial location. This may represent the ability to construct a basic mental map, consisting of both general spatial layout and salient objects, which is then a key feature of the overall test. An analysis of the AD group alone indicated that video location was chiefly important, as well as free recall; the two together explained 80% of the variance. It is not certain that the video clips were more easily processed or used by the AD group than the tasks using still photos, as they were able to repeat the video clips to create longer effective exposures. It is interesting that video location was one of the most difficult tasks overall, judging from group performance levels. The importance of free recall in the AD group may simply reflect their very poor performance in this area, making it useful in discriminating them as a group.

The factor analysis done using the various spatial orientation tests showed two basic factors. The first, comprising all tasks pertaining to knowledge of the route per se, was the largest and explained nearly half the variance. The second factor was made up of the two recall tests, and explained 15% of the variance. While there was some cross loading on the two factors, it is clear that the spatial navigation and location tests that are key subtests for the spatial orientation battery of tests and are not simply versions of episodic learning and memory tasks, as they demonstrated a clear separation upon factor analysis.

Further analysis of the free recall responses sought to determine what proportion were recalled consecutively, that is, named in the order they were found on the actual route. In this way, one might further infer the presence of a kind of mental map, if a given participant listed objects as if mentally making a trip around the route. Since recall was not directed, this would reflect only spontaneous use of this strategy. It was therefore impressive that approximately 30% of normal subjects used this strategy, with a fair amount of variance seen. In terms of the AD group, very few items were recalled in general, but only about 1% of these reflected any mental ordering. Further, AD subjects most often named only the most recently or currently seen objects, showing expected difficulty with acquisition as well as rapid forgetting.

The analysis of the data from the spatial orientation battery of tests also included an analysis of series of neuropsychological tests, involving memory as well as several chosen to relate to perceptual judgment, mental rotations and visual memory. It is often useful to examine the degree of overlap between known behavioral and cognitive tests and a newly developed one. In a stepwise regression predicting spatial orientation test scores, 3 neuropsychological measures were chosen. Given the spatial nature of the tasks, this is not surprising. The particular tasks chosen show an interesting relationship with the spatial orientation test. The Road Map test is known to tap direction sense and mental spatial reversals; the Figural Memory test relates to memory for novel visual information; Judgment of Line Orientation pertains to perception of visuospatial detail. The degree of overlap, as indicated by the remainder of 62% of variance left unexplained, indicates that the spatial orientation test provides significant and unique information regarding spatial navigation skills beyond that derived from several standard neuropsychological tests.

The three neuropsychological tests that emerged from the regression analysis also had the highest correlations with total spatial orientation test scores. This underscores the fact that the spatial orientation test according to embodiments of the present invention has the desired property of correlating most highly with spatially- and perceptually-based tasks, and is the foundation for a demonstration of convergent validity. At the same time, minimal correlations with memory measures or the MMSE suggest divergent validity, with the spatial orientation test not being a general measure of cognitive or memory ability.

An interesting pattern was seen when these same neuropsychological tests were correlated with a key spatial orientation tests, photo location, separately for each participant group. In all three normal groups, the expected correlations between photo location and the three neuropsychological tests obtain, suggesting the known degree of overlap between the components of the photo location task and the diverse neuropsychological abilities tapped by the three measures. In the AD group, however, the three significant correlations are replaced by just one, that involving Judgment of Line Orientation. This indicates, first of all, that the underlying strategies used by the AD subjects may have narrowed considerably. It further suggests that the strategy being relied on is a purely perceptual one, as the line orientation task requires only direct angular and spatial matching.

So, while uniform progression is the prevailing view, and while verbal figural memory are not predictive of functional independence, the spatial orientation battery of tests of the present invention provide new instruments for measuring spatial orientation capacities. The new instruments for measuring spatial orientation capacities as are provided by the present invention, when administered to human subjects provided results that indicate that the navigational capacity of normal subjects is good; and that the same capacity was impaired in AD subjects. Furthermore, the spatial orientation battery of tests indicate that the impairment is not a memory-based impairment.

As will be understood by those of skill in the art, the present invention may be practiced in other specific forms without departing from the essential characteristics thereof. For example, the predetermined path can take any shape having a plurality of segments and turning points. Or that the spatial orientation battery of tests may include only a subset of the test described above, or all of the tests. Furthermore, the order in which the tests are administered may be varied to suit particular assessment scenarios. Accordingly, the foregoing is intended to be illustrative, but not limiting of the scope of the invention, which is set forth in the following claims.

What is claimed is:

1. A method for assessing the navigational capacity in a human subject, comprising:
   taking the subject on a course of a predetermined path in a natural or naturalistic virtual environment, wherein said path comprises a plurality of turning points;
   conducting a navigation test comprising asking the subject questions that compose items on a plurality of navigation subtests concerning said path and environment;
   recording with a computer the subject's response to said questions as navigation subtest scores and the sum of the subtest scores as a total navigation test score, thus transforming the subject's response to said questions that are representative of a navigation capacity into navigation subtest scores and a total navigation test score;
   analyzing with a computer said test scores obtained in an identified patient or subject population to create an analyzed result that characterizes the navigation capacities of that population, thus transforming said subtest scores into analyzed results that are representative of navigation capacity, and correlating said analyzed results with a profile for a neurological disorder; and
   assessing with a computer the subject's navigational capacity using said analyzed result, wherein navigational capacity includes the variety of abilities defined by the plurality of navigation subtests,
   wherein said navigation test comprises a route learning subtest comprising
   initiating to retake the subject on a subject-directed course of said path;
   while retaking the subject on said path asking the subject whether the subject had previously gone left, right or forward at each of said plurality of turning points;
   recording the subject's response to said asking;
   determining whether said response is correct;
   if the subject's response concerning each of said turning points is incorrect, then correcting the subject's response to maintain the integrity of said path; and
   continuing to retake the subject on said path, while continuing said asking, said recording and said determining until said subject has completed said path.

2. The method of claim 1 wherein said taking comprises taking the subject on said path in a natural environment with the subject passively transported while seated in a wheeled chair.

3. The method of claim 1 further comprising an object recall subtest comprising
   asking the subject to name only those objects or landmarks that were helpful to the subject in following said path on said subject-directed course.

4. The method of claim 1 further comprising a free recall subtest comprising:
   allocating a period of time; and
   asking the subject to name as many objects or landmarks as the subject is able to recall from said path in said period of time.

5. The method of claim 4 further comprising scoring the subject's response to said asking depending on the number of said objects or landmarks and the order of said objects or landmarks with respect to the sequence in which said objects or landmarks were encountered by the subject on said path.

6. The method of claim 4 wherein said period of time is between 30 seconds and 5 minutes.

7. The method of claim 1 wherein said navigation test comprises a route drawing subtest comprising
   moving the subject to an area away from said path;
   providing the subject with a first scaled outline drawing of said environment;
   showing the subject a landmark from said path on said first outline;
   asking the subject to mark the starting point of said path on said first scaled outline;
   thereafter providing the subject with a second scaled outline showing the correct location of said starting point and asking the subject to draw a line on said second outline from said starting point to show the first segment of said path;
   continuing to provide the subject with a subsequent outline, showing said starting point and said previous segment including said first segment, and asking the subject to draw the next line segment representing the next segment of said path on said subsequent outline, wherein said subsequent outline is one of a plurality of outlines, each showing the next segment of said path that the subject was taken on; and
   continuing said showing and said asking until the subject has completed the drawing of said path in its entirety on a final scaled outline of said plurality of outlines.

8. The method of claim 1 wherein said navigation test comprises an image recognition subtest comprising
   presenting the subject with a plurality of images, wherein said plurality of images comprise a first plurality of images depicting scenes from the subject's view of said path and a second plurality of images depicting scenes from the subject's view of scenes other than from said path;

asking the subject to identify whether each one of said plurality of images was an image depicting a scene from said path; and scoring the subject's answer to said asking depending on whether each one of said plurality of images was correctly identified by the subject as being from said path or not.

9. The method of claim 8 wherein said presenting is a computer-based presenting.

10. The method of claim 1,
wherein said navigation test comprises an image location subtest comprising
presenting the subject with an image depicting a scene from the subject's view of said path;
providing the subject with a scaled drawing of said environment;
asking the subject to match said image with a location on said scaled drawing of said path;
scoring the subject's answer to said asking depending on whether said image was correctly matched with a correct location on said scaled drawing.

11. The method of claim 10 wherein said image is one of a plurality of images, wherein each of said plurality of images comprise an image depicting a scene from the subject's view of said path.

12. The method of claim 10 wherein said presenting is a computer-based presenting.

13. The method of claim 1,
wherein said navigation test comprises a video location subtest comprising
presenting the subject with a video clip wherein said video clip comprises video images depicting scenes from the subject's view of said path;
providing the subject with a scaled drawing of said environment; and
asking the subject to identify the location on said scaled drawing that corresponds with said video clip.

14. The method of claim 13 wherein said asking comprises asking the subject to identify the location on said scaled drawing where said video clip begins.

15. The method of claim 13 wherein said asking comprises asking the subject to identify where the subject was moving in said video clip on said scaled drawing.

16. The method of claim 13 wherein said asking comprises asking the subject to identify the location on said scaled drawing where said video clip ends.

17. The method of claim 13 wherein said video clip image is one of a plurality of video clips, wherein each of said plurality of video clips comprises video images depicting a scene from the subject's view of said path.

18. The method of claim 1 wherein said analyzing comprises a statistical analysis of neuropsychological data describing a patient or subject population.

19. The method of claim 18 wherein said statistical analysis comprises one of a correlation analysis, a regression analysis, a multi-factor analysis, a principal component analysis, a multivariate analysis of variance analysis (MANOVA), or a combination thereof.

20. The method of claim 18 wherein said statistical analysis comprises a regression analysis predicting how well a profile for assessing a neurodegenerative disorder predicts navigational capacity based on the test scores.

21. The method of claim 1 wherein the neurological disorder comprises Alzheimer's disease and its subtypes and variants.

22. A method for assessing the navigational capacity in a human subject, comprising:
taking the subject on a course of a predetermined path in a natural or naturalistic virtual environment, wherein said path comprises a plurality of turning points;
conducting a navigation test comprising asking the subject questions that compose items on a plurality of navigation subtests concerning said path and environment;
recording with a computer the subject's response to said questions as navigation subtest scores and the sum of the subtest scores as a total navigation test score, thus transforming the subject's response to said questions that are representative of a navigation capacity into navigation subtest scores and a total navigation test score;
analyzing with a computer said test scores obtained in an identified patient or subject population to create an analyzed result that characterizes the navigation capacities of that population, thus transforming said subtest scores into analyzed results that are representative of navigation capacity, and correlating said analyzed results with a profile for a neurological disorder; and
assessing with a computer the subject's navigational capacity using said analyzed result, wherein navigational capacity includes the variety of abilities defined by the plurality of navigation subtests,
wherein said navigation test comprises a self-orientation subtest comprising
maintaining the subject at a starting point of said path;
showing the subject a plurality of images of objects or locations taken from said path;
asking the subject to point in the direction of the location of each of said plurality of objects or locations, as if there were no walls between the subject and said location;
classifying the subject's response as correct if the direction pointed to by the subject is within +/−22.5 degrees of said location.

23. The method of claim 22 wherein said showing is a computer-based showing.

* * * * *